United States Patent [19]

Mintz

[11] Patent Number: 4,867,738
[45] Date of Patent: Sep. 19, 1989

[54] APPARATUS AND METHODS FOR UTILIZING AUTOTRANSFUSION SYSTEMS AND RELATED EQUIPMENT

[75] Inventor: Michael D. Mintz, Edison, N.J.

[73] Assignee: International Technidyne Corporation, Edison, N.J.

[21] Appl. No.: 93,050

[22] Filed: Sep. 14, 1987

[51] Int. Cl.⁴ .......................................... A61M 37/00
[52] U.S. Cl. ...................................... 604/4; 206/459; 206/430
[58] Field of Search ....................... 604/4–6, 604/30–31, 269, 266, 403, 406, 407; 206/363, 438, 459

[56] References Cited

U.S. PATENT DOCUMENTS

| | | | |
|---|---|---|---|
| 3,690,315 | 9/1972 | Chittenden et al. | 206/363 |
| 3,989,046 | 11/1976 | Pannier, Jr. et al. | 604/319 |
| 4,014,329 | 3/1977 | Welch et al. | 604/406 |
| 4,300,551 | 11/1981 | Kinney | 604/5 |
| 4,479,761 | 10/1984 | Bilstad et al. | 604/6 |
| 4,545,783 | 10/1985 | Vaughn | 206/438 |
| 4,547,186 | 10/1985 | Bartlett | 604/4 |
| 4,655,197 | 4/1987 | Atkinson | 604/30 |

OTHER PUBLICATIONS

Waterless Thoracic Drainage, Atrium Medical Corporation, 4 pages, 1983.

Primary Examiner—C. Fred Rosenbaum
Assistant Examiner—Kathleen A. Daley
Attorney, Agent, or Firm—Arthur L. Plevy

[57] ABSTRACT

There is disclosed an autotransfusion system which essentially is contained in a unitary housing section which enables a practitioner to utilize the system in a rapid and efficient manner. The housing section has integrally associated therewith a blood reservoir, which is a major component of an autotransfusion system. The housing has secured thereto a set of instructions which are adapted to be mounted on the arm of an IV pole and which, when positioned on the arm of the IV pole, specifies vertical distances necessary to perform autotransfusion during a blood collection or blood distribution mode. The housing section, as containing the reservoir, with the package and instruction component, is used as a yardstick to establish specified distances in order to control pressure as afforded by gravity. The entire unit lends itself to the rapid installation of an autotransfusion system while providing visual instructions which are integrally associated therewith to provide users with operational guidance that is thereby readily available during an operative procedure. The housing further permits pre-assembly and sterilization of the various components of an autotransfusion system.

1 Claim, 5 Drawing Sheets

APPARATUS AND METHODS FOR UTILIZING AUTOTRANSFUSION SYSTEMS AND RELATED EQUIPMENT

BACKGROUND OF THE INVENTION

This invention relates to body fluid delivery systems and more particularly to an autotransfusion system which is integrally incorporated for easy use during an operative procedure.

The prior art contains many examples of autotransfusion systems which generally operate as follows.

An autotransfusion system essentially is a self-contained disposable system for intra-operative collection, anticoagulation, filtration and reinfusion of blood shed into body cavities. The system employs a special suction wand which incorporates a citrate-phosphate-dextrose (CPD) anticoagulant metering system. The system is used to collect blood which flows into a blood reservoir or cardiology reservoir. The blood reservoir may be connected to a blood bag which is used to deliver the blood to the patient via an extension set which contains a microemboli filter, while simultaneously permitting continued blood collection in the blood reservoir.

Such systems have been employed in many situations and have been found to be completely effective and essentially an important part of certain surgical procedures. For example, the system is used where the patient experiences rapid blood loss, where there is an unavailability of appropriate bank blood or in surgery in which the complications of bank blood must be avoided. The systems can be further employed in conjunction with cell washing autotransfusion devices or where the patient's religious convictions precludes the use of bank blood.

As indicated, such systems have been described extensively in the prior art. See, for example, the following U.S. Patents.

U.S. Pat. No. 4,547,186 issued to R. H. Bartlett entitled "Autotransfusion System" and dated Oct. 15, 1985. This patent describes a system for autotransfusion where the surgeon uses an aspirating wand or tube coupled to a vacuum source through a reservoir for receiving aspirated blood. From that reservoir blood flows to a receiving bag in a relatively low position below the elevation of the patient. When there is sufficient blood supply in the bag the bag is elevated from its lower position to a point higher than the patient. Blood then flows from the elevated bag, by gravity or externally applied pressure, through a conducting tube and a needle into the patient. When the bag is then substantially emptied, it is again lowered to an elevation lower than the blood reservoir for repetition of the operation. If desired, an anticoagulant can be introduced into the aspirated blood. As one can ascertain from the above-noted patent, the system is described and comprises a multiplicity of connecting tubes and various other devices which are associated with an IV pole which supports the system.

U.S. Pat. No. 4,540,406 issued on Sept. 10, 1985 to C. Miles and entitled "Anticoagulant Delivery System For Use With An Autotransfusion System". In that patent, anticoagulant is added to blood being aspirated through a hand-held wand having an venturi throat. The anticoagulant flows into the wand from a generally closed anticoagulant reservoir, which is higher than the wand, as replacement air flows into the anticoagulant air reservoir. This allows air inflow to be controlled by a regulator which is fixed on the wand and in accordance with the amount of aspirated blood flowing in through the venturi throat. The patent also shows an autotransfusion system of the type that this present invention is concerned with.

U.S. Pat. No. 4,551,131 issued on Nov. 5, 1985 to C. Miles and entitled "Autotransfusion System With Anticoagulant Delivery System". That patent shows a movable aspiration wand which carries a tank for anticoagulant which is replenished from an anticoagulant source fixed at a high elevation and is connected to a blood reservoir at a low elevation. Differences in wand height relative to the source and to the blood reservoir are compensated for so that differences in wand height and corresponding blood and anticoagulant height do not substantially vary the anticoagulant portion added to the aspirated blood. In any event, schematics and drawings concerning that system are also shown.

As one can ascertain from the above-noted references autotransfusion systems have been employed in the prior art. As one will also ascertain, such systems are relatively complex and require a great deal of set up time in order to utilize the systems. Based on the nature of such systems, the individual components are bulky, such as the blood reservoir and other components. These components, as one can ascertain from the above prior art, have to be coupled together via various tubes and other devices so that the system maintains an operable position. Such set up procedures are extremely prolonged and instruction manuals for operating and setting up such systems are extensive.

In any event, the prior art has experienced a great deal of difficulty in utilizing such systems due to the difficulties in connecting such systems together.

In this respect, it is an object of the present invention to provide an autotransfusion system which, due to the nature of its packaging, will enable one to utilize the system components in a simple and reliable manner. The particular packaging and utilization of an autotransfusion system, according to the teachings of this invention, saves a great deal of expensive labor time and, further, fully assures that the system is set up in a proper and reliable manner, and that sterility of system components is assured throughout the unpacking, set-up and utilization procedures.

The technique for packaging such a system further insures that various heights, levels and so on are automatically maintained and provides a simple means for allowing an unskilled laborer to set a system up prior to an operative procedure. The packaging, as described, serves as an integral part of the system and is adapted to be mounted directly on an intravenous (IV) pole. By means of the packaging, which includes a procedure chart, a relatively inexperienced practitioner can set up the system in a simple and reliable manner. It is further noted that the packaging also allows for the easy transportation of such systems. For example, from a source of distribution to hospitals and various other facilities which employ such systems in the ordinary course of business.

BRIEF DESCRIPTION OF PREFERRED EMBODIMENT

A system of the type employed for body fluid processing for the selective transfer of body fluid, using gravity or externally applied pressure, to a patient which fluid transfer system is positioned on a conventional intravenous pole (IV) with said system associated with a body fluid reservoir having inlet and outlet ports for implementing said transfer and adapted to operate with additional fluid containing reservoirs positioned on said pole, the combination therewith of apparatus for maintaining and orienting said fluid system in an operative configuration on said pole, comprising a housing having an opened top surface and a closed bottom surface and having contiguous sidewalls for forming a component cavity, a fluid reservoir permanently affixed to said housing and positioned in said cavity, means coupled to said housing for securing said housing to said pole, and a foldable indicia carrying means secured to said housing and adapted when unfolded to coact with the cross arm of said pole to thereby position said reservoir as secured to said housing at an optimum location on said pole to assure proper fluid transfer.

DETAILED DESCRIPTION

Figure 1:
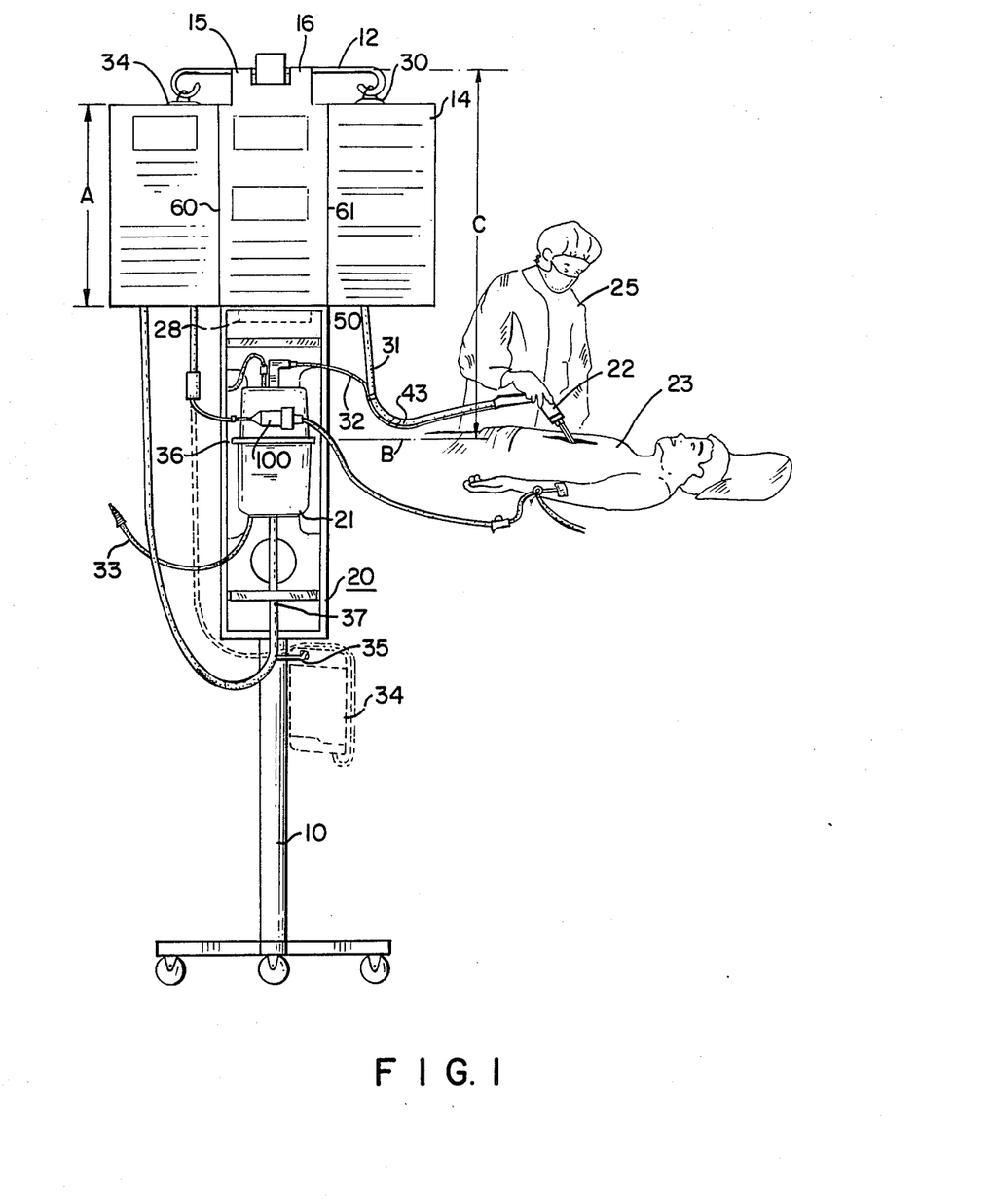
FIG. 1 is a plan view of an autotransfusion system according to this invention and further showing an operative procedure being performed by a surgeon.

Referring to FIG. 1 there is shown a general schematic of an autotransfusion system incorporating apparatus according to the teachings of this invention. As seen in FIG. 1 there is a surgeon 25 who is performing an operative procedure on a patient 23. The surgeon is holding in his hand a suction wand 22 which enables the surgeon to perform blood aspiration. The wand may provide automatic mixing with an anticoagulant, which anticoagulant is obtained from a source 30. The source 30 may be a CPD anticoagulant bottle which is suspended from the IV pole by means of the extending cross arm or hanger 12 associated with conventional IV pole 10. As seen, the entire system, including those in the prior art, are used in conjunction with a typical IV pole 10. As shown in the figure, there is associated with the system a various number of tubes. For example, the aspirator, or wand 22, is coupled to the source of anticoagulant via a tube 31. It is also coupled via a tube 32 to a blood reservoir 21. The reservoir 21 is also coupled via a tube 33 to a source of vacuum in order to provide the necessary air pressures for operating the wand. Also seen in FIG. 1, suspended from the hanger 12 of the IV pole 10, is a blood bag 34 which is shown in its raised position.

In this manner the system depicted in FIG. 1 is an autotransfusion system whereby the blood bag in the position as shown is positioned for delivery of blood to a patient. In any event, the blood reservoir 21 is also associated with, and has located thereon, a hook as 35. This hook, or coupling mechanism, can accommodate the blood bag 34 in a lower position which enables the blood bag to be filled during an operative procedure.

As one can ascertain from FIG. 1, there are man tubes associated with the particular system, which tubes must be employed in order to provide proper system coupling. According to prior art techniques, the coupling of the various devices, such as the blood reservoir 21, the suction wand 22 to various sources of blood and anticoagulant, as well as to suitable vacuum sources and so on, was a relatively complicated procedure. According to the teachings of this invention and as seen in FIG. 1, a blood reservoir 21 is integrally formed in or integrally secured to a housing module 20. The housing module 20 has secured thereto a complete set of directions 14 for outlining in detail the operation and connections to the system. The directions 14 are imprinted on a foldable billboard 14 which is firmly secured to the rear of the package or housing assembly 20 by an extending bottom flap 28. The height of the billboard, designated by A, is dimensioned so that once the tabs 15 and 16 are secured about the arm 12 the main reservoir 21 is exactly positioned at the proper patient level B to enable the entire system to operate both in a blood delivery mode or a blood collection mode.

It is noted that the system mainly operates on gravity as anticoagulant source 30 has to be at a predetermined distance with respect to the reservoir 21, and the elevation of suction handle 22 must also be within a specified zone above or below reservoir 21. Essentially, the elevation of the reservoir 21 is determined by the exact patient position. As seen in FIG. 1, since the housing 20 is integrally part of the billboard or instruction sheet 14, the distance A is accurately determined as is the distance of the reservoir 21 with respect to arm 12 of IV pole 10. Thus, by manually adjusting the elevation C of arm 12 with respect to patient 23, the elevation of reservoir 21 with respect to patient 23 may be set to a specified value, zero for example.

As will be explained, the housing 20 contains many other features which enables a manufacturer to completely package an entire system whereby the instruction or bulletin 14 is integrally secured to the housing assembly so that the set up procedure for such a system becomes extremely simple. It is noted that the housing 20 is secured to the IV pole 10, as will be further described.

There are other features of the housing which adapt themselves to enable one to utilize the autotransfusion system in a simple and reliable manner both for operative procedures and for storage and transport.

As one skilled in the art will further ascertain, the system of FIG. 1 may consist of a combination of standard off-the-shelf components that are used in such autotransfusion systems. The hand-held blood suction wand 22 is normally connected via a first lumen of a tri-lumen PVC tube 43 to the blood reservoir 21. The reservoir 21 in turn is connected to an appropriately regulated vacuum source via tube 33 which provides suction at the tip of the wand 22. Blood aspirated with the suction handle 22 is mixed with the anticoagulant, which is retained in bottle 30 and is drawn via the tube 31 and a second lumen of PVC tube 43. The blood/anticoagulant mixture is thereafter drawn through the first lumen to the reservoir 21.

A third lumen of tri-lumen PVC tube 43 is connected to anticoagulant bottle 30 in a manner to allow entry of a controlled flow of air thereby to displace and control the flow of anticoagulant from bottle 30 to the blood/anticoagulant mixing point in suction handle 22. A second end of the third lumen is connected to valving means contained within suction handle 22 that modulates the entry of ambient air into the third lumen. The valving means in turn co-acts with the flow of blood entering suction handle 22 in a manner to modulate the ambient air flow in direct proportion to the amount of blood entering and passing through suction handle 22.

As the anticoagulated blood flows into the reservoir 21, it is defoamed and filtered using a gross filter which is incorporated in the standard reservoir 21. This collected blood falls by gravity through a one-way valve to a blood bag as 34 (dashed position). When filled the blood bag 34 is raised, as shown in FIG. 1, to deliver the blood, by gravity or externally applied pressure, through a one-way valve and through an optional blood microfilter 100 to the patient via a venuous catheter. Because of the one way valve between the reservoir and blood bag, retrograde flow of blood into the reservoir is prevented and blood suction at the .bleeding site can continue without being interrupted by the process of blood infusion. The one-way valve and the venuous infusion line prevents retrograde flow of blood from the patient. As appropriate during use, the blood bag 34 is alternately lowered for filling from the reservoir 21 via line 37 and then raised for blood infusion to the patient. The bag 34 is shown in solid and dashed line positions.

Figure 2:
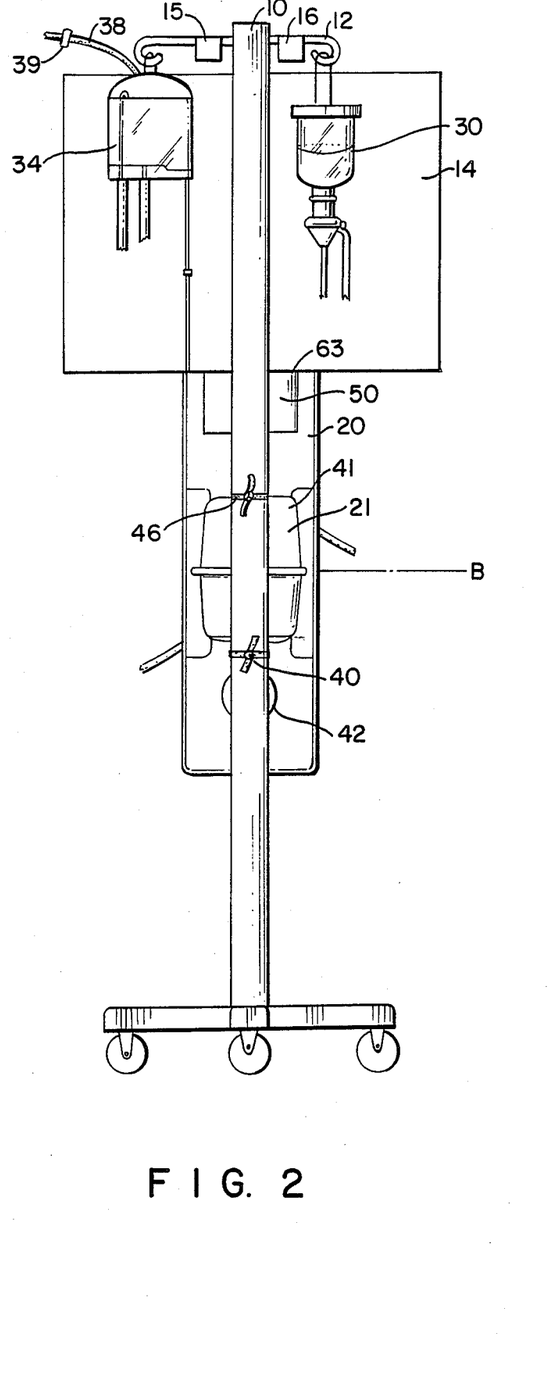
FIG. 2 is a rear view of the autotransfusion system of FIG. necessary to show certain features according to this invention.

The system may also include a separate tube 38 connected at the top of blood bag 34 and passing through a one-way valve to reservoir 21. A tubing clamp 39 ordinarily inhibits flow through the tube 38 (FIG. 2). However, prior to infusion of the contents of blood bag 34 into patient 23, the tubing clamp 39 is removed, and air, which may have passed with the blood into bag 34, is drawn by the vacuum through tube 38 into reservoir 21. After replacing the tubing clamp 39, the bag 34 is properly hung on arm 12 of IV pole 10 for subsequent patient infusion, without the danger of air embolism.

As indicated, the above description is indicative of typical operation of prior art autotransfusion devices. As one can immediately ascertain, the system contains a number of discrete components with a plurality of tubes which tubing, as well as the components, must be properly connected to operate properly.

A further important consideration is the fact that the reservoir level, as indicated by B, must be accurately ascertained as well as the positions of both the blood bag 34 and the CPD bottle. Since the system operates with gravity feed, the height of the arm 12 with respect to the patient level must be accurately maintained.

As will be further described, due to the construction of the housing 20, and in combination with the instruction board 14, these positions are accurately provided by the apparatus of this invention. It is further completely understood that since the instructions 14 are an integral part of the housing 20, which housing 20 is firmly secured to the IV pole, then there is no problem during an operative procedure for a practitioner to look at the instructions as they are immediately available in the event that one of the tubes becomes dislodged or in the event of a system failure. As one will immediately ascertain, in all prior art systems, an instruction manual, which was an extensive document, was packaged separately with the individual components. Thus, based on prior art devices, if the system failed or tubing or another device became dislodged the practitioner may not have access to the manual and, hence, the autotransfusion system, with its appended advantages, had to be eliminated. Thus, there are many practitioners who were reluctant to use such systems because of the operational and connection complexities and the above problems.

With the above in mind, and as one can further ascertain, the system has many components associated therewith and consists of many tubes in order to provide optimum coupling.

Referring to FIG. 2 there is shown a rear view of the apparatus shown in FIG. 1. The same reference numerals have been retained for clarity. FIG. 2 also eliminates the various tubing connections which, as indicated above, are part and parcel of the prior art. In any event, the housing 20 is shown in a rear view. As will be explained, the housing 20 consists of a bottom portion which essentially is thermoformed or molded utilizing a suitable plastic, such as a typical styrene or other plastic. The housing is molded so that it has a central portion 41 which is contoured to the outer dimensions of a typical blood reservoir. Blood reservoir, as reservoir 21 of FIG. 1, is a standard component and can be purchased from may different sources. The blood reservoir, as will be further explained, is secured within the housing 20 by means of a suitable glue or epoxy so that once secured it cannot be moved.

As shown in FIG. 2, the entire housing section 20 is tied by means of suitable tie members 40 and 46 to the IV pole 10. The directions are imprinted on the foldable billboard 14, which billboard 14 is secured firmly to the housing 20 by means of a flap 50 which flap 50 is inserted within an upper indentation performed in the housing section 20. The bulletin, as seen both in FIGS. 1 and 2, has scored lines or fold lines as, for example, 60 and 61 of FIG. 1 which enables the bulletin to be folded as a book and then folded via line 63 so that it is flush against the rear of the housing and is integrally attached thereto. The height A, or length of the bulletin 14 or instruction sheet 14, is such that the arm 12 of the IV pole 10 may be manually positioned in a preferred position with respect to the patient level B once the extending flaps 15 and 16 of bulletin 14 are wrapped and secured about the arm 12 of the IV pole. The flaps 15 and 16, as shown in FIGS. 1 and 2, are extending tabs which are integrally formed with the instruction bulletin 14 and have Velcro pads or other means on appropriate sides to enable the exact coupling of both tabs 15 and 16 to the arm 12 of the IV pole. In this manner, the positioning of the reservoir 21 is accurately known and is indicative of the patient level B as shown in both FIGS. 1 and 2. This, therefore, eliminates all guessing for the set up procedure and, hence, enables one to rapidly perform coupling of each and every device and component by means of the instruction bulletin or instruction directory 14, which is secured t the housing section 20 and which further operates to define the exact patient level, as well as the suitable level for both the blood bag 34 and the CPD bottle 30.

As indicated in the employment of prior art autotransfusion systems, the center ridge 36 (FIG. 1), associated with the reservoir 21, should be positioned and maintained at the aspiration site level throughout the entire procedure. In this manner the suction wand 22 should only be used within a wand operating zone which is normally defined by suitable visual markers which also are implemented on the package housing 20.

It is also important that the resulting distance between the hanger 12 and the blood reservoir 21 must be maintained for proper functioning of the device. This distance is automatically ascertained by the dimension A associated with the integrally formed instruction bulletin 14.

Essentially, as indicated, suppliers of such prior art systems package the various components necessary for autotransfusion operation in a box or container. The box was associated with a suitable manual and the entire system had to be assembled based on those directions in the manual. Such prior art systems included various devices, such as wires and other measuring devices, which would enable the set-up procedure to be implemented. In any event, the entire process was extremely time consuming and oftentimes resulted in an inoperative system. For example of such instructions reference is made to a publication entitled "Enhanced Features of the BloodStat Autotransfusion System" published by Thoratec Medical, Incorporated of Berkeley, Calif. on Dec. 17, 1985. Thus, as one can ascertain from FIGS. 1 and 2, the incorporation of the blood reservoir, as integrally secured to a preformed housing section 20 which is associated with a predetermined set of directions on a foldable board 14, completely determines all the necessary operating levels for the entire system. The housing 20 is then secured directly to the IV pole and is secured at a distance so that the board 14 is in the position, for example, shown in FIGS. 1 or 2. In this manner, the blood bag 34, as well as the CPD reservoir 30, can then be supported on the arm 12 of the IV pole and the system is thus set at the exact proper height.

The instructions regarding tubing connections to the various devices, including the filters and valves as briefly outlined above, are all depicted on the bulletin board 14 which is always in full view during the entire operating procedure. This, therefore, enables a rapid repair of any system malfunction because the instructions are integrally part of this particular system. Thus, as can be seen, the housing 20 is pole mountable. It is particularly tailored to the product. The packaging and documentation are integrally formed as well as the package and instruction components 14 are employed as a yardstick to establish a specified distance necessary to control pressure operation via gravity.

Furthermore, the housing 20 is employed as both a storage and shipping device means as will be further explained. Hence, the housing 20 serves a complete three-phase purpose. It serves in the capacity as indicated above, as being pole mountable, while serving as part of an extremely reliable and rugged storage container which can be utilized for the sterile storage and transport of such systems by all modes of transportation, as will be further described. It also permits the manufacturer to pre-connect the various components and tubes, thereby simplifying and facilitating initial emergency set-up of the system.

Figure 3:
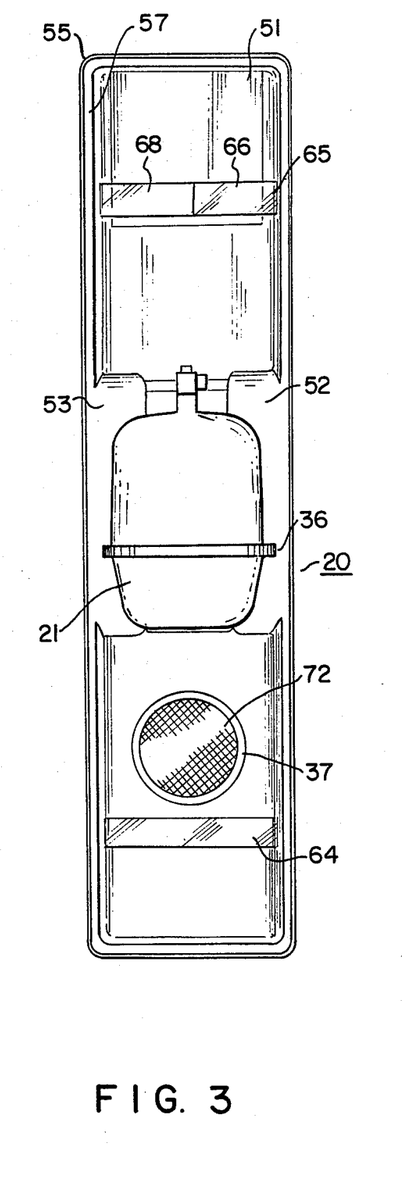
FIG. 3 is a top plan view of a housing section according to this invention.
Figure 4:
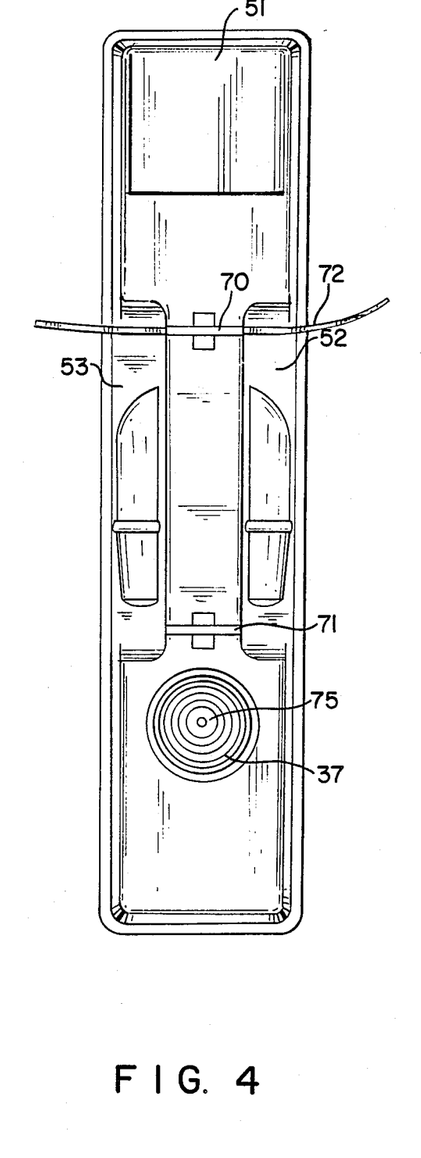
FIG. 4 is a bottom plan view of the housing section.

Referring to FIGS. 3 and 4, there is respectively shown a top plan view and a bottom plan view of the housing section 20, as shown in FIGS. 1 and 2. The housing 20 is generally a rectangular box-like structure having an opened top surface, closed bottom surface and extending sidewalls to form a component containing cavity. There are show cross bars or cross members 64 and 65 which serve as supports to strengthen the housing 20 and to further retain additional components above and below the reservoir 21. The supports 60 and 64 may be planar plastic members and can be removed at will.

As seen from FIG. 3, the housing section 20 has two integrally formed or molded support members 52 and 53. Each member is formed during a suitable molding process so that each member conforms to the outer shape of the blood reservoir 21 and has a corresponding adjacent channel to accommodate the peripheral flange 36 of the blood reservoir 21. The blood reservoir 21 is therefore conformally cradled between support members 52 and 53 with peripheral flange 36 emplaced within the channels associated with members 52 and 53 and is then firmly secured to the same. Securing of the blood reservoir 21, which again as indicated is a conventional component, is accomplished by means of a suitable epoxy or glue and, hence, the blood reservoir 21 is firmly emplaced within the housing section 20. The length of the housing section 20 is, of course, predetermined.

Located on the underside of the housing section, as seen in FIG. 4, is a recessed rectangular area 51 which accommodates the bottom extending tab 50 associated with the instruction sheet 14. In this manner the bottom tab 50 of the instruction sheet is firmly glued or secured within area 51, thus making the package and instruction component 14 an integral part of the housing section 20.

Also seen in FIG. 3 is that the housing section 20 has an internal peripheral flange 57 which essentially is bordered by an extending flange 55. The housing 20 also includes an integral recessed area 37 which essentially is premolded into the plastic and is provided to accommodate a filter media disc 72. As seen in FIG. 4, recess 37 consists of a concentric arrangement of raised portions with a central aperture 75. The inside of recessed area 37 is then covered with a suitable filter material 72. The filter material 72, as well as the aperture 75, assure that the entire unit, when covered by a cover member, is properly vented to atmospheric pressure while it is completely isolated from contaminants in the external environment. Essentially, the filter 72 can comprise many different materials, such as a typical lidding material, a non-woven filter material, as those materials employed in conventional medical packaging. Suitable materials are sold under the brand name of Tyvek.

Referring to FIG. 4 there is shown, as indicated, a bottom plan view of the package housing section 20. As seen in FIG. 4 there are two channels 70 and 71 where both channels accommodate a suitable tying material or a string or lQ ribbon material 72. The channel 71 also includes such a tying material 72, which is firmly glued or otherwise secured within the channels 70 and 71 and which, as shown in FIG. 2 (40 and 46), operates to firmly tie the entire housing section 20 to the IV pole 10. These strips may be fabricated from a plurality of suitable type materials, as should be obvious to those skilled in the art.

Figure 5:
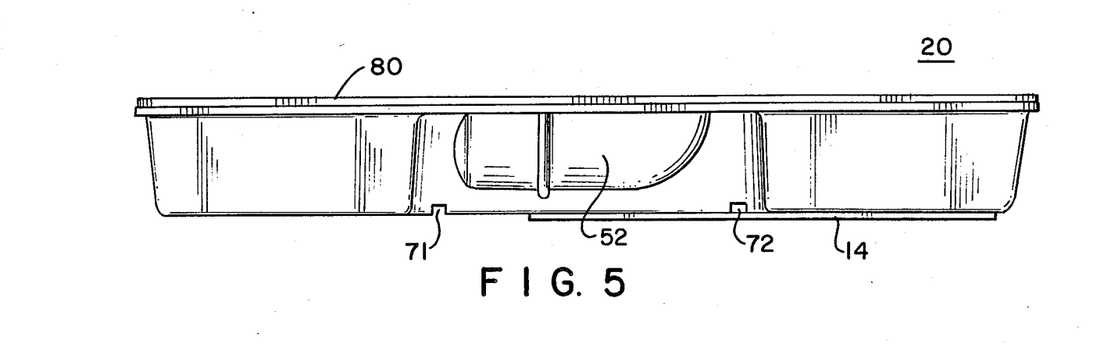
FIG. 5 is a side plan view of the housing section.

Referring to FIG. 5 there is shown a side view of the housing 20. As one can see from FIG. 5, the channels 70 and 71 are essentially formed by the molding process in the U bottom surface of the housing section 20. The housing section 20 has an extending peripheral flange 80, as is more clearly depicted in the side view of FIG. 5. As indicated above, the entire housing section 20 is fabricated by a thermoform process employing molds and plastic and may be, for example, made of polystyrene or another suitable material.

Figure 6:
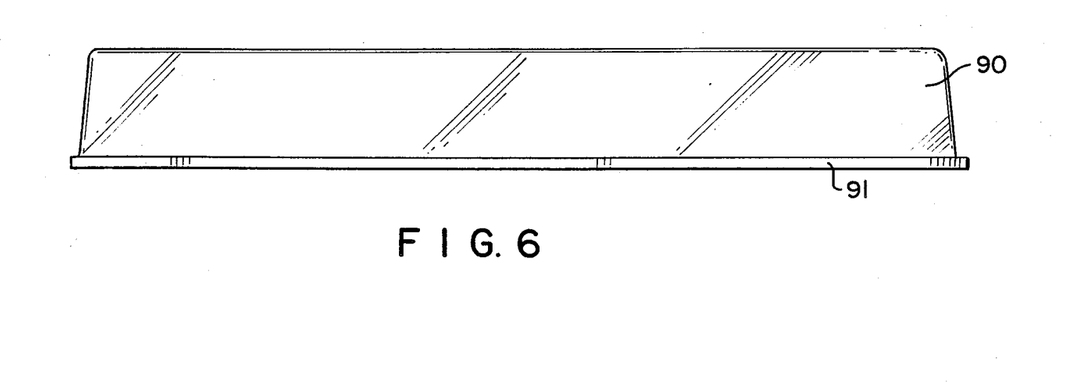
FIG. 6 is a side plan view of a cover member.

FIG. 6 shows a cover member 90. The cover member 90 is fabricated from a clear plastic material, such as a PETG plastic, and essentially is also formed by a molding U process. The cover member 90 has an outer peripheral flange 91 which is adapted to coact with the extending flange 80 associated with housing section 20.

Figure 7:
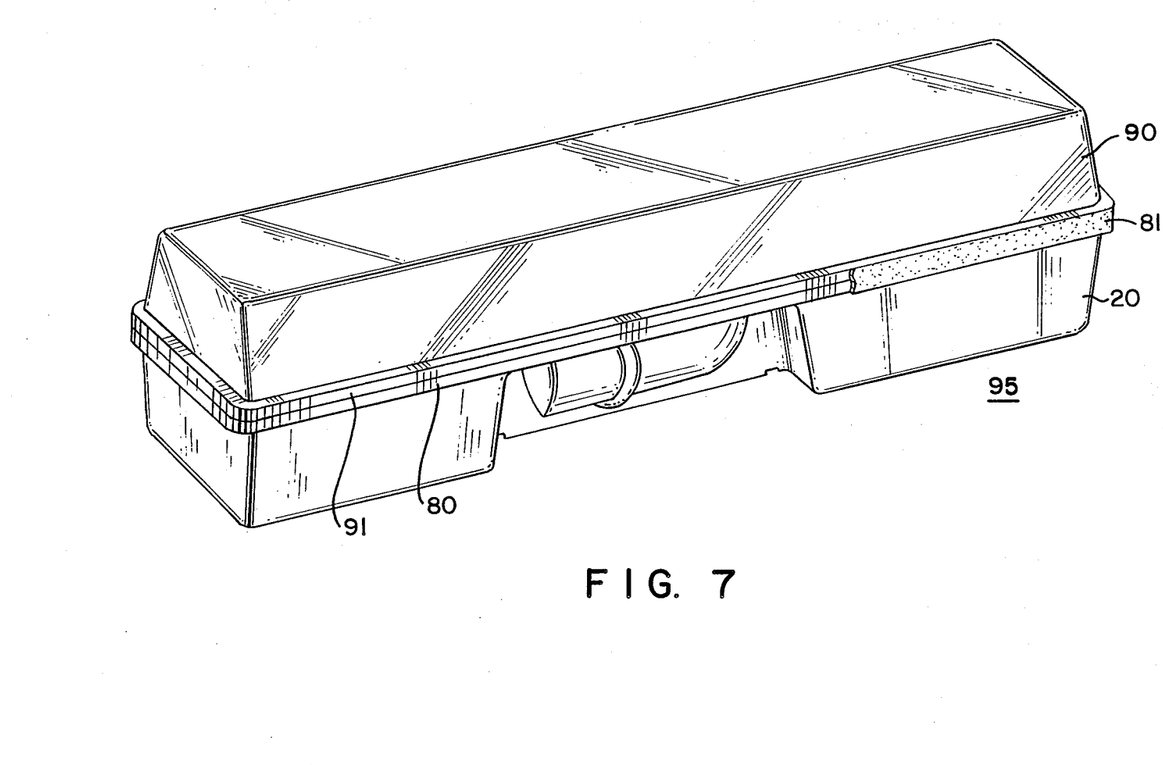
FIG. 7 is a prospective plan view of the cover member of FIG. 6 coupled to the housing section of FIG. 5.

Referring to FIG. 7 there is shown a perspective view of the cover member 90 coupled to the housing section 20 whereby the flange 91 completely encircles the depending flange 80 of section 20. Once the entire assembly is provided with all the necessary components, the entire package is sealed by means of a suitable plastic tape or other material 81 which provides a removable proper sterile and mechanical seal. The filter 72, including the aperture, enables any pressure pertubations to be compensated for by allowing the inside atmosphere of the entire packaging container to adapt to any corresponding outside pressure. In this manner such systems can be delivered by aircraft or various modes of transportation without fear of distortion to the package 95 or contamination of its contents. Hence, the entire unit can be sterilized with the filter and suitable filtering materials serving to maintain sterilization and to provide pressure equalization.

As one can see from FIG. 7, once the unit is received in an operating room the set up procedure is extremely simple. In preparation for emergency use, housing section 20 is tied to the IV pole 10 with the directions, as affixed thereto, now extended as unfolded and hung. This, again, establishes all proper operating conditions while the package and instruction components serve as a yardstick to establish the specified important distances necessary to U control pressure during autotransfusion operations. When an auto transfusion procedure is actually needed, the IV pole 10 with attached closed package 95 is brought to the actual site of the operational procedure. Tape 81 is then removed and plastic cover 90 disposed of, thereby exposing the sterile, preassembled autotransfusion system contained therein, as shown for example in FIG. 1.

As one can ascertain from FIG. 3, the housing section 20 also serves as a storage means. Thus, the support bar, as 64 and 65, operate in conjunction with various tapes, 00 as 66 and 68, or various tying members to secure additional system components. As one will ascertain, the entire system, together with the integral reservoir 21, is shipped to a suitable facility with other additional components which are normally necessary to implement the entire system construction as, for example, shown in FIG. 1. Hence, the remaining portions of the housing section 20, for example those portions above and below the reservoir 21, may contain at least the following components. Thus, the housing section 20 will contain assisting tubing which can, for example, be attached to the reservoir 21 via the suitable inlet and outlet ports. It may also contain the filter, as shown in FIG. 1 and designated by reference numeral 100. It is noted, of course, that the components, as described in FIG. 1, may be conventional off-the-shelf components and, hence, the components contained in a package may be selected according to the preferences of a particular user. It is also understood that the package assembly or section 20 contains a suction wand, the instrument pouch, suction tips and various other units which are associated with the autotransfusion system as shown in FIG. 1.

Thus, as will be apparent to those skilled in the art, the housing section 20 forms an integral unit which is integrally associated with the blood reservoir 21 and which housing serves to be pole mounted so that the proper distances, as necessary for gravity operation, are all accurately maintained. This is based on the integral formation of the housing, together with the instruction directory 14. It should be thus apparent that the above-noted concept will enable one to utilize autotransfusion systems in a simplified manner while further affording many advantages which were not available in prior art techniques. The housing 20 further physically protects the reservoir 21 and other system components which may be of fragile construction. Hence, if the pole 10 were upset or banged into another object, the housing 20 acts as a protective barrier as well as a main component of such a system. While particular concentration has been made in regard to autotransfusion systems the concept can be employed with other body fluid processing systems such as renal dialysis systems and so on.

What is claimed is:

1. In a system of the type employed for body fluid processing for the selective transfer of body fluid to a patient using gravity or external pressure which fluid transfer system is positioned on a conventional intravenous pole (IV) with said system associated with a body fluid reservoir having inlet and outlet ports for implementing said transfer and adapted to operate with additional fluid containing reservoirs positioned on said pole, the combination therewith of apparatus for maintaining and orienting said fluid system in an operative configuration on sale pole, comprising:

a housing having an opened top surface and a closed bottom surface and having contiguous sidewalls for forming a component cavity;

a fluid reservoir permanently affixed to said housing and positioned in said cavity;

means coupled to said housing for securing said housing to said pole;

a foldable indicia carrying means secured to said housing and adapted when unfolded to coact with the cross arm of said pole to thereby position said reservoir as secured to said housing at an optimum location on said pole to assure proper fluid transfer, said folding indicia carrying means having a central planar section with foldable right and left sheet sections, each capable of folding over said central section, with said central section being relatively congruent with a portion of said bottom surface such that when said right and left sheet sections are folded over said central section, said central section can then be folded to overlie said bottom surface of said housing section during storage or transport, said foldable indicia carrying means having an extending bottom tab secured to the bottom surface of said housing and at least one top extending tab adapted to encircle the cross arm of an IV pole and having a length for positioning said reservoir at an optimum level for autotransfusion procedures.

* * * * *